United States Patent
Meskens (10) Patent No.: US 8,634,773 B2
(45) Date of Patent: Jan. 21, 2014

(54) SHORT RANGE COMMUNICATIONS FOR BODY CONTACTING DEVICES

(75) Inventor: Werner Meskens, Opwijk (BE)

(73) Assignee: Cochlear Limited, NSW (AU)

(*) Notice: Subject to any disclaimer, the term of this patent is extended or adjusted under 35 U.S.C. 154(b) by 1084 days.

(21) Appl. No.: 12/251,453

(22) Filed: Oct. 14, 2008

(65) Prior Publication Data

US 2009/0124201 A1 May 14, 2009

(30) Foreign Application Priority Data

Oct. 12, 2007 (AU) ................ 2007905584

(51) Int. Cl.
*H04B 7/00* (2006.01)

(52) U.S. Cl.
USPC .................... 455/41.2; 455/41.3

(58) Field of Classification Search
USPC ........... 455/41.1, 41.2, 41.3, 575.1, 575.6, 455/90.1–90.3, 550.1, 569; 381/328, 330, 381/380, 381
See application file for complete search history.

(56) References Cited

U.S. PATENT DOCUMENTS

| | | | |
|---|---|---|---|
| 4,654,880 A * | 3/1987 | Sontag .................. | 455/41.2 |
| 4,741,339 A | 5/1988 | Harrison et al. | |
| 5,914,701 A | 6/1999 | Gersheneld et al. | |
| 6,115,636 A | 9/2000 | Ryan | |
| 6,223,018 B1 | 4/2001 | Fukumoto et al. | |
| 6,574,510 B2 | 6/2003 | Von Arx et al. | |
| 6,748,094 B1 | 6/2004 | Tziviskos et al. | |
| 6,766,201 B2 | 7/2004 | Von Arx et al. | |
| 6,924,773 B1 | 8/2005 | Paratte | |
| 7,020,298 B1 | 3/2006 | Tziviskos et al. | |
| 7,088,267 B2 | 8/2006 | Tajima | |
| 7,171,177 B2 | 1/2007 | Park et al. | |
| 7,181,024 B1 | 2/2007 | Oba et al. | |
| 7,206,423 B1 | 4/2007 | Feng et al. | |
| 7,392,091 B2 | 6/2008 | Bruinsma | |
| 7,406,105 B2 * | 7/2008 | DelMain et al. ............ | 370/519 |
| 2004/0138723 A1 | 7/2004 | Malick et al. | |
| 2004/0202339 A1 | 10/2004 | O'Brien, Jr. et al. | |
| 2009/0030488 A1 | 1/2009 | Bruinsma | |

FOREIGN PATENT DOCUMENTS

| | | |
|---|---|---|
| AU | 2002218936 | 9/2002 |
| AU | 2005201357 | 10/2005 |

OTHER PUBLICATIONS

Examiner's First Report on Australian Patent Application No. 2004240245 by Cochlear Limited. Mailed Feb. 12, 2009.

* cited by examiner

*Primary Examiner* — Eugene Yun
(74) *Attorney, Agent, or Firm* — Kilpatrick, Townsend & Stockton, LLP.

(57) ABSTRACT

A communication system for wirelessly transmitting at least one signal, the system comprising: a first device configured to receive and modulate the at least one signal, the first device having a first conductive element operatively adapted to contact a first human body and a second conductive element isolated from the first human body, wherein the first and second elements operate to wirelessly transmit the modulated signal; and a second device having a first conductive element operatively adapted to contact a second human body, and a second conductive element isolated from the second human body, wherein the first and second elements operate to receive the transmitted modulated signal from the first device.

23 Claims, 8 Drawing Sheets

SHORT RANGE COMMUNICATIONS FOR BODY CONTACTING DEVICES

CROSS-REFERENCE TO RELATED APPLICATIONS

This application claims priority from Australian Provisional Application No. 2007905584, filed Oct. 12, 2007, entitled "Short range communications for body contacting devices". The above application is hereby incorporated by reference herein.

BACKGROUND

1. Field of the Invention

The present invention relates to short range communication systems, apparatus and methods using the human body and air as a medium, for example for medical devices and partially implantable medical systems.

2. Related Art

In many applications, it is necessary for devices located near, on, or within the human body to communicate with each other. For example, a partially implantable device may need to transmit and receive data from another externally located device near or on the body, or several devices may need to exchange information. Wired communications are reliable, but may not be aesthetically pleasing, or practical.

Conventional near field, radio frequency communications experience various practical issues in such applications. Conventional RF communications in particular experience relatively large power losses when transmitting across the body.

One proposal to address this is the use of electrostatic fields. Such arrangements are disclosed in T. G. Zimmerman, "Personal Area Networks: Near-field intra-body communication" (IBM Systems Journal, vol. 35, No. 3&4, 1986, pp. 609-617), and in U.S. Pat. No. 5,914,701. Zimmerman's method makes use of two electrodes per device, and forms two separate signal routes between the human body and an earth ground. This creates issues if the earth ground and human body ground are brought in to contact.

U.S. Pat. No. 6,223,018 to Fukumoto discloses a communication device using a time varying electric or electrostatic field with a carrier frequency from several tens of KHz to several MHz.

Other short range wireless communication methods and systems are based upon generating and capturing the potential difference signal in a frequency band such that a quasi-electrostatic field formed within the human body is dominant over a radiation field formed outside the human body when the transmitting electrode and the receiving electrode are each disposed in very close vicinity to the human body. For example, U.S. Pat. No. 7,181,024 to Oba et al discloses an arrangement for use with a personal audio apparatus. Body contact electrodes are associated with the headphones and the playback apparatus. The audio signal is modulated onto a carrier frequency of 2 to 30 MHz. U.S. Pat. No. 6,118,882 to Haynes discloses the use of radio frequency signals transmitted through the human body to communicate between a base device and earphones, wherein each earpiece advantageously includes a coil.

SUMMARY

In one aspect of the present invention a communication system for wirelessly transmitting at least one signal is provided. The system comprises: a first device configured to receive and modulate the at least one signal, the first device having a first conductive element operatively adapted to contact a first human body and a second conductive element isolated from the first human body, wherein the first and second elements operate to wirelessly transmit the modulated signal; and a second device having a first conductive element operatively adapted to contact a second human body, and a second conductive element isolated from the second human body, wherein the first and second elements operate to receive the transmitted modulated signal from the first device.

In another aspect of the present invention a transmitter for wirelessly transmitting at least one signal to a receiver is provided. The transmitter comprises a first module configured to receive the at least one signal; a second module configured to modulate the at least one signal; and a third module comprising: a first conductive element operatively adapted to contact a human body, and a second conductive element conductively isolated from the human body, wherein the first and second elements operate to wirelessly transmit the modulated signal to the receiver.

In another aspect of the present invention a method for wireless communication between a first device and a second device is provided. The method comprises: receiving at least one signal at the first device for transmission to the second device; modulating at the first device the at least one signal; and wirelessly transmitting to the second device the modulated signal via first and second conductive elements, the first conductive element contacting a human body and a second conductive element isolated from the human body.

BRIEF DESCRIPTION OF THE DRAWINGS

Illustrative embodiments of the present invention are described herein with reference to the accompanying drawings, in which.

DETAILED DESCRIPTION

Aspects of the present invention are generally directed to a short range communication system utilizing a human body to enable transmission of at least one signal from a first device to a second device. The first device receives and modulates the at least one signal and wirelessly transmits the modulated signal to the second device. Specifically, the first device has a first conductive element operatively adapted to contact a first human body, and a second conductive element isolated from the first human body which to wirelessly transmit the modulated signal to the second device. The second device comprises a first conductive element operatively adapted to contact a second human body, and a second conductive element isolated from the second human body, which operate to receive the transmitted modulated signal from the first device. The second device is configured to demodulate the received signal and to output the at least one signal.

Embodiments of the present invention will now be described with reference to specific embodiments. It will be appreciated that embodiments of the present invention may be implemented through a wide variety of components, structures and conductive elements. As such, the embodiments of the present invention described herein should be considered as illustrative and do not limit the present invention in any manner.

It will be further understood that embodiments of the present invention provide a communications system which may be widely applied. In a specific application, the communication system is implemented in a medical device system, such as a hearing prosthesis. Hearing prosthesis include, but are not limited to, hearing aids, cochlear implants, brain stem implants, middle ear implants, electro-acoustic devices, combinations thereof, whether fully, partly of completely implanted, and any other such devices. Embodiments of the present invention may provide communications between external and implanted components, as well as between multiple external and/or internal devices.

Embodiments of the present invention may also be applied to other medical devices, for example sensors and monitoring systems, other implanted devices, to provide communications between devices, and any other similar applications. Embodiments may be further applied to other uses close to the human body, for example for personal audio devices, earpieces or other accessories for mobile telephones, body worn accessories or sensors, and similar applications.

Near-field intra-body communication devices based upon electrostatic fields operate in relative low frequency bands (<<30 MHz) where the distance between devices is typically smaller than one wavelength $\lambda$ or even smaller than $\lambda/2\pi$. Operation at higher frequency channels (>30 MHz) would mean that for the same physical separation of the intra-body communication devices, the propagation distance becomes equal to a multiple of the wavelengths. In this case the radiated field or even far-field electromagnetic wave propagation could characterize such an intrabody communication link.

Figure 8:
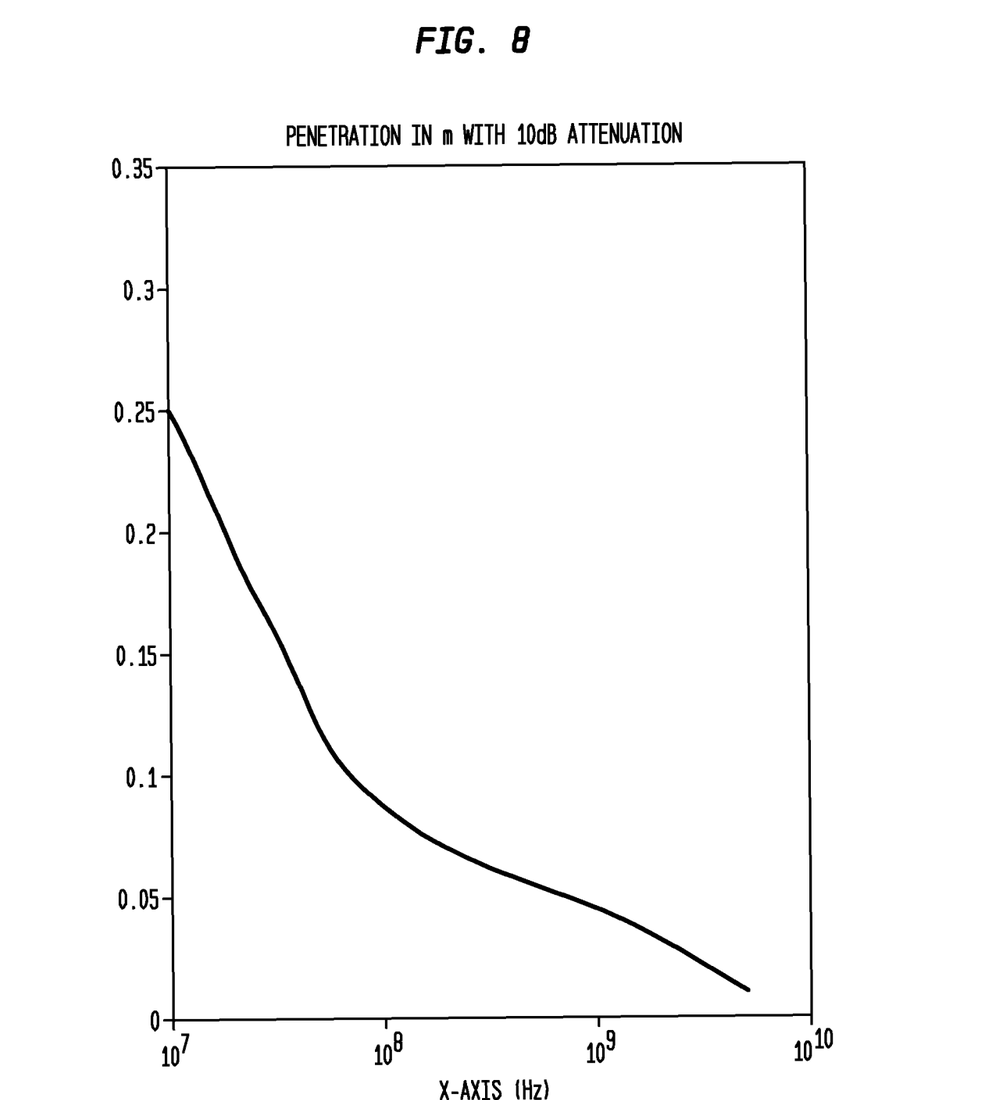
FIG. 8 shows a graph illustrating signal penetration losses for human tissue.

RF signal losses in intrabody and near body applications are understood as principally due to the finite electrical resistivity of the human body causing energy dissipation or penetration losses (absorption) inside the body. These penetration losses increase as frequency increases. Therefore, it is conventionally assumed that establishing an intra-body communication link at higher frequencies channels would be quite power demanding, because conventional. FIG. 8 shows penetration losses for human tissue, in m with 10 dB attenuation. Penetration in meters appears on the vertical axis, with frequency on the horizontal axis.

Consider the case of a link between two behind the ear (BTE) devices at 400 MHz. The shortest communication path consists of mainly human tissue. When the bilateral devices are separated 18 cm from each other, 30 dB additional penetration loss (10 dB/6 cm) occurs, as shown in FIG. 8. If the frequency is increased to 2.4 GHz (millimeter waves), then there would be a 65 dB (10 dB/2.5 cm) penetration loss. As such, it may be beneficial to operate wireless transmission in the decimeter and/or centimeter frequency bands. For example, the frequency range may be from about 50 to about 500 MHz.

The human body itself may also act as a portion of an antenna for electromagnetic waves. This may be partially explained by the skin-effect, and by the electrical conductivity of tissue, organs and blood. The skin effect is the description given to the phenomenon where electromagnetic fields (and therefore the current) decay rapidly with depth inside a good conductor. The earliest work on explaining the skin effect was done by Lord Kelvin in 1887. Tesla also investigated the effect.

This means that if we attach and electrically connect an RF communication device to the human body, conduction of the RF signal by the human body is mainly present outside the body. This explains how the human body itself may act as a portion of an antenna for electromagnetic waves.

Figure 1:
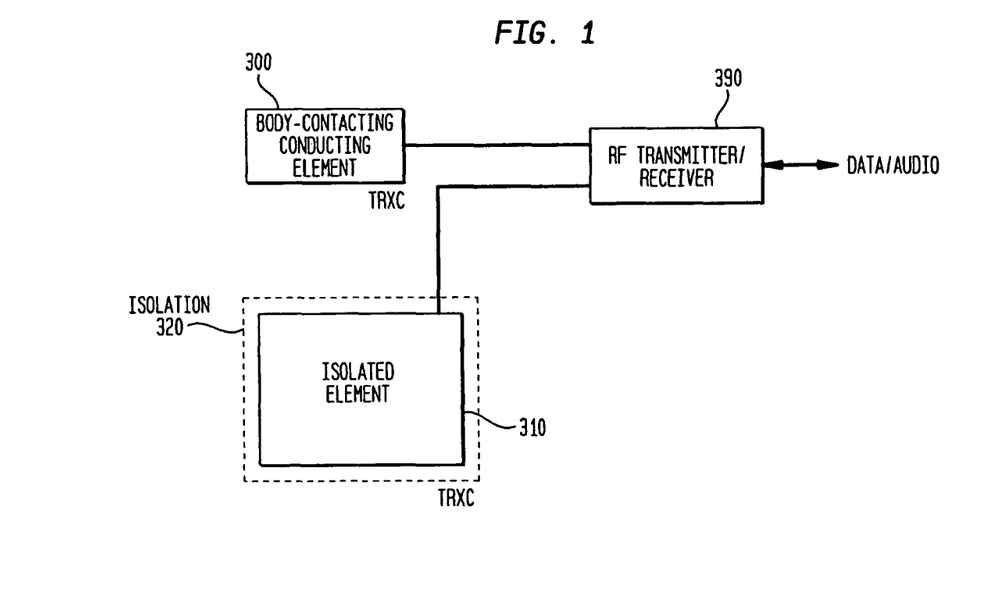
FIG. 1 is a simplified schematic diagram of the transceiver part of a device belonging to a short range communication system.
Figure 2:
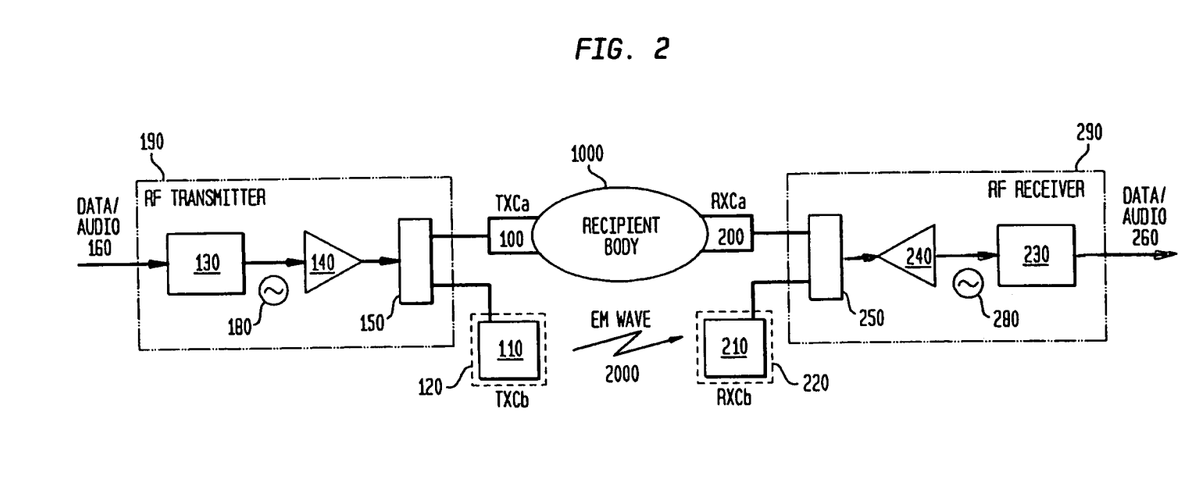
FIG. 2 is a schematic diagram of a transmitter part of a first device and receiver part of a second device belonging to a short range communication system.

FIG. 1 illustrates a general schematic view of a transceiver according to embodiments of the present invention. RF transmitter/receiver module 390 sends and receives signals via the conducting element 300 in contact with the body, and the isolated element 310. The isolated conductive element 310 is shown with an isolation 320. A time varying RF signal is output via the elements 300, 310, as well as received via these elements. The conductive elements are preferably coupled via an impedance matching circuit as known in the art. For example, in one embodiment a balun 150, 250 may be included in the receiver/transmitter 390 as shown in FIG. 2 to connect conducting element 300 and isolated element 310. That is, inputs and outputs are symmetrically coupled. It will be appreciated that in some circumstances the device may only transmit, or only receive.

In principle, first conducting element 300 attached to the body functions as an imperfect ground plane of an antenna while second conducting element 310, which is isolated from the body, functions as the radiating element of that same antenna.

In certain embodiments, radiating element 310 as shown in FIG. 1 may be considered as a small open-ended/monopole antenna with a ground-plane connection element 300. When the radiating element 310 (with a length of 2 cm) is kept small compared to the wavelength at the operating frequency the short-range communication has electromagnetic far-field characteristics. The power for a plane wave in the far field rolls-off inversely proportionally to the square of the distance from the source.

Not only this roll-off factor, but also shadowing effects or tissue absorptions caused by the human body increase the total path loss or link attenuation.

The area (and shape) of the surfaces used in the elements 300, 310 is (are) mainly determined by the application. The distance of the extreme borders of the shape should be much smaller than a quarter wavelength.

The conductive elements 300 making contact with the human body may be made from non-allergic and non-toxic materials or metals (e.g. titanium or its alloys, platinum, or gold). The conductive surface isolated from the human body may be made from any electrically conductive material such as copper (for example, the PCB groundplane).

The operative surfaces of the contact element 300 (ground) and isolated surface 310 (radiating element) may be collocated in a same plane (e.g. FIG. 1) or in parallel planes (e.g. similar to a patch antenna). Whilst a good degree of isolation 320 (i.e. electrical resistance) of the isolated surface 310 relative to the contact element 300 is desirable, use of 'high' isolation is not required.

It is noted that an implant with a suitable antenna configuration could communicate with the external device attached to the human body, noting the tissue attenuation described in FIG. 8.

FIG. 2 illustrates in more detail an implementation of a transmitter and of a separate receiver, according to embodiments of the present invention. The RF transmitter stage 190 receives the data, audio or other signal 160. This is modulated 130 onto the carrier signal 180, processed by RF stage 140, and presented to a balun and matching element 150, for presentation to each element 100, 110. Element 100 is in contact with the body 1000; element 110 is isolated 120 from the body.

As noted above, element 150 functions as an impedance matching circuit. Element 150 may comprise a balun combiner and/or other components as known in the art. As would be appreciated, a balun is a passive electronic device that converts between balanced and unbalanced electrical signals. The balun is used to change impedance. Baluns may be considered as simple forms of transmission line transformers.

The signal propagates both through the body 1000, and through the air via the skin effect as previously discussed 2000. At the receiver stage 290, the signal is received by conductive elements 200, 210 similar to the transmitter stage. The element signals pass through the balun and matching element 250, to the RF stage 240, before demodulation 230 relative to the known carrier signal 280. The signal 260 is then presented for use by the device as required.

It will be appreciated that the details of implementation of the electronic components represent well understood systems by those skilled in the art, and consequently these will not be explained in great detail.

The RF stage 140, 240 will vary somewhat depending upon the type of modulation, carrier frequency, and so forth selected. In general, it will include on both the transmitter side and receiver side an amplifier, filters, and up and down converters. The modulation and demodulation components may be of any suitable type, for example using RLC circuitry or ceramic resonators (e.g. quadrature detector—frequency demodulation—FM), phase locked loops (e.g. Frequency or phase modulation/demodulation—FM, PM), or diodes (e.g. envelope detector—Amplitude demodulation—AM), or any other suitable digital or analog system. It is preferred that a relatively simple modulation scheme, for example an ASK system with an NRZ line coding scheme, is used to minimise the processing burden upon the devices. Similarly, any suitable arrangement for generating a carrier signal could be used.

The balun 150, 250 operates to convert symmetrical to asymmetrical RF feeding points (or vice versa) for the conducting elements. The matching components are generally a passive LC circuit to match the impedance of the input to the output so as to minimise signal losses.

Figure 3:
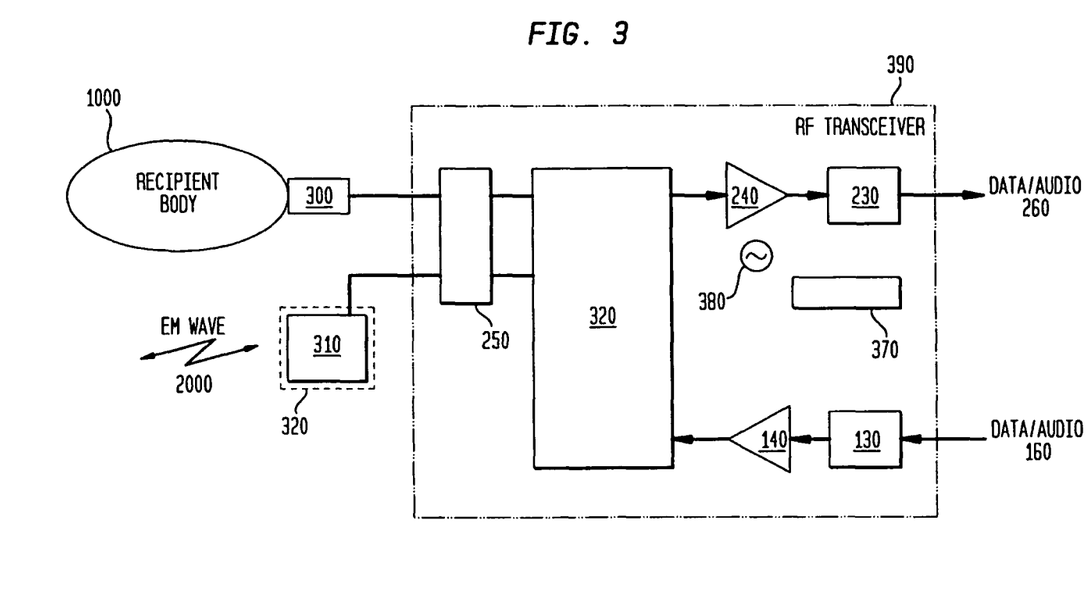
FIG. 3 is a schematic diagram of the transceiver part of a device belonging to a short range communication system.

FIG. 3 is a schematic diagram of the transceiver part of a device belonging to a short range communication system. In this arrangement, many of the components are common with FIG. 2, and will not be described again in detail. Note that the signal generator 380 is shared by the transmitter and receiver stages. Both the transmitter and receiver stages interface with the common conducting elements 300, 310 via the RF combiner 320. The RF combiner 320 (or RF switch) couples the receiver and transmitter stages to the common conducting elements. This RF combiner 320 guarantees a high RF isolation between the receiver and transmitter stages, necessary to avoid impedance mismatches and receiver saturation, and optimizing RF energy transfer between common conducting elements and receiver/transmitter. Also included is an interface to the wireless controller mechanism 370.

Figure 4A:
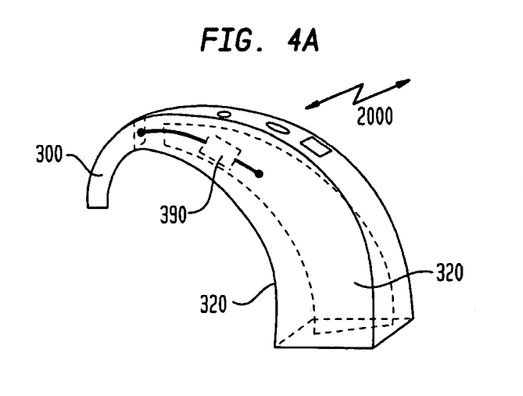
FIG. 4A is a side view of a behind-the-ear device of a hearing aid communication system.

FIG. 4A illustrates a BTE device for use with a hearing aid, cochlear implant or other hearing prosthesis. The device 320 includes a conductive plate 300 in contact with the user's body, and an isolated element 310 within the device and isolated from the user's body. A transmitter device 390 is operative to use the plate 300 and element 310 to transmit audio, or processed audio of some type. This may be to a bilateral device to facilitate (for example) timing or input selection; to a device which provides processing of the audio; or to an implanted device, for example a cochlear implant. The precise nature of processing in the BTE device of the audio, or the use of this once received, are not limited by the present invention.

Figure 4B:
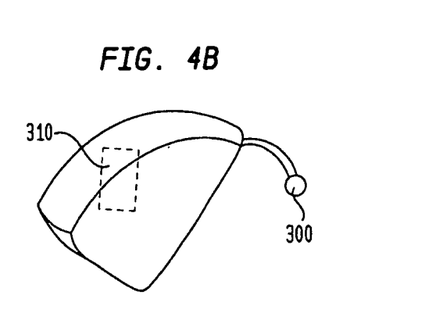
FIG. 4B is a side view of a micro-behind-the-ear device of a hearing aid communication system including a conductive earhook.
Figure 4C:
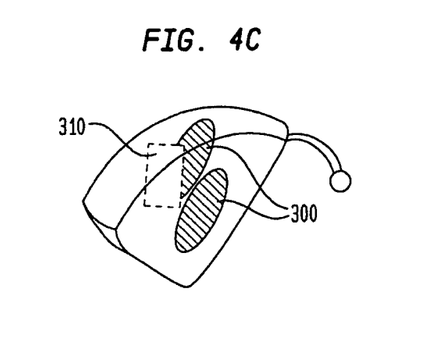
FIG. 4C is a side view of a micro-behind-the-ear device of a hearing aid communication system including conductive surfaces.

FIGS. 4B and 4B illustrate further embodiments of the present invention in micro-BTE devices, with contact element 300 and isolated element 310.

Figure 4D:
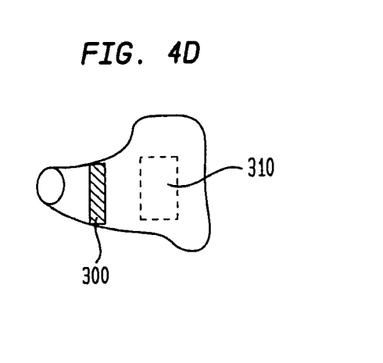
FIG. 4D is a side view of an in-the-ear device of a hearing aid communication system.

It will be understood that the BTE implementation is only one possibility. Embodiments of the present invention could equally, in this context, be applied to a device which is body worn, or totally or partially in the ear canal as shown in FIG. 4D with contact element 300 and isolated element 310. It could also be employed for communications between one or more implanted devices, and one or more external devices. A particular advantage of the present implementation is that the device is symmetrical, in that the same antenna design works for the left or right ear.

Figure 5:
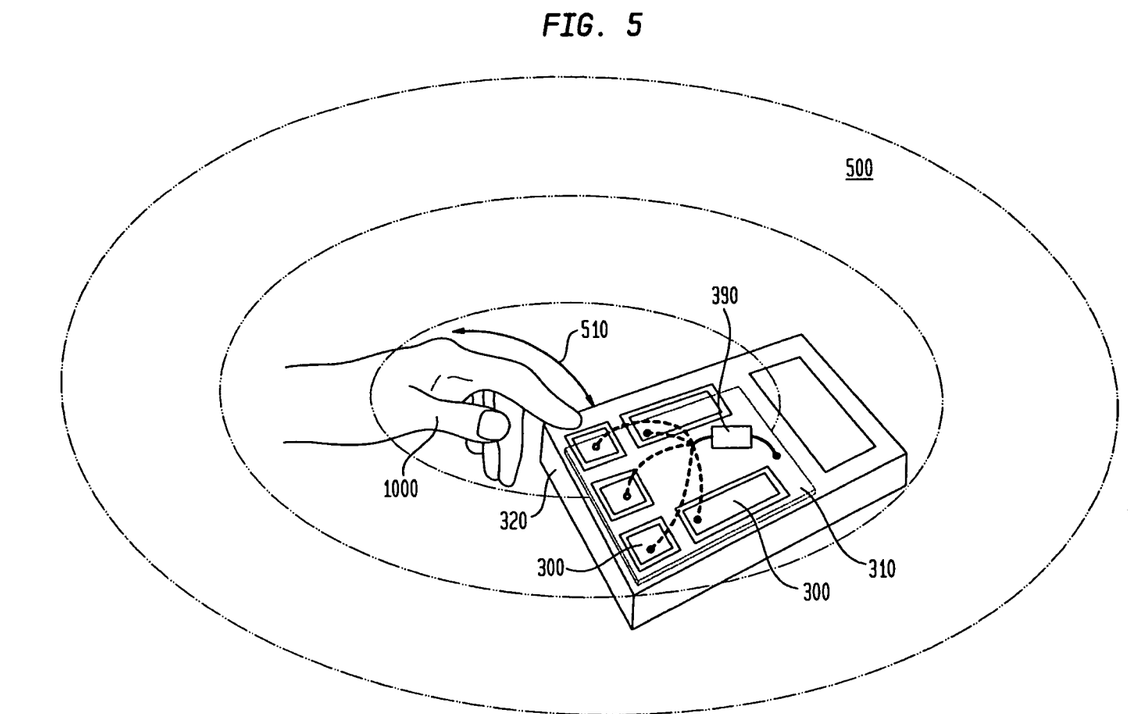
FIG. 5 is a perspective view of the remote control unit of a short range communication system.
Figure 6:
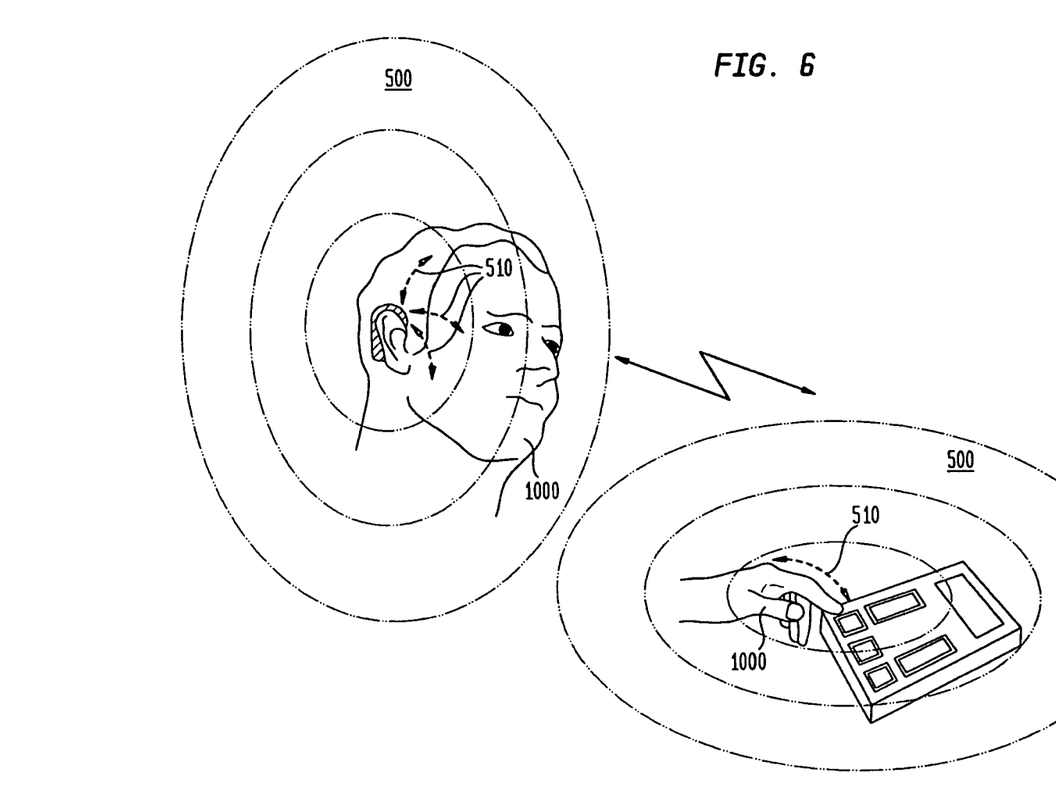
FIG. 6 is a perspective view of a behind-the-ear device and the remote control unit of a short range communication system.

FIG. 5 illustrates a possible wireless controller device, for example of the general type used to control digital hearing aids and the like. As illustrated, there are two specific substantial phenomena allowing efficient communications between a control device and any other body-worn device. One phenomenon is the electromagnetic field propagation 500 radiated through the air between the wireless controller device and other body-worn devices; a second phenomenon is conduction 510 via contact between the user's hand or fingers, and the controller 390. It will be appreciated that there is a direct conduction path between the BTE device, via the contact element 300 and the body 1000, to the controller 390. From the perspective of embodiments of the present invention, the face of the controller forms the body contact element 300 for the controller 390, with an isolate element 310 within the isolated 320 body of the controller. This arrangement is further illustrated by FIG. 6, which shows the conductions and radiation paths from the BTE device. So a portion of the human body such as a finger touching a conductive key on a wireless controller device could be used as a portion of an EM (electromagnetic) antenna.

Figure 7:
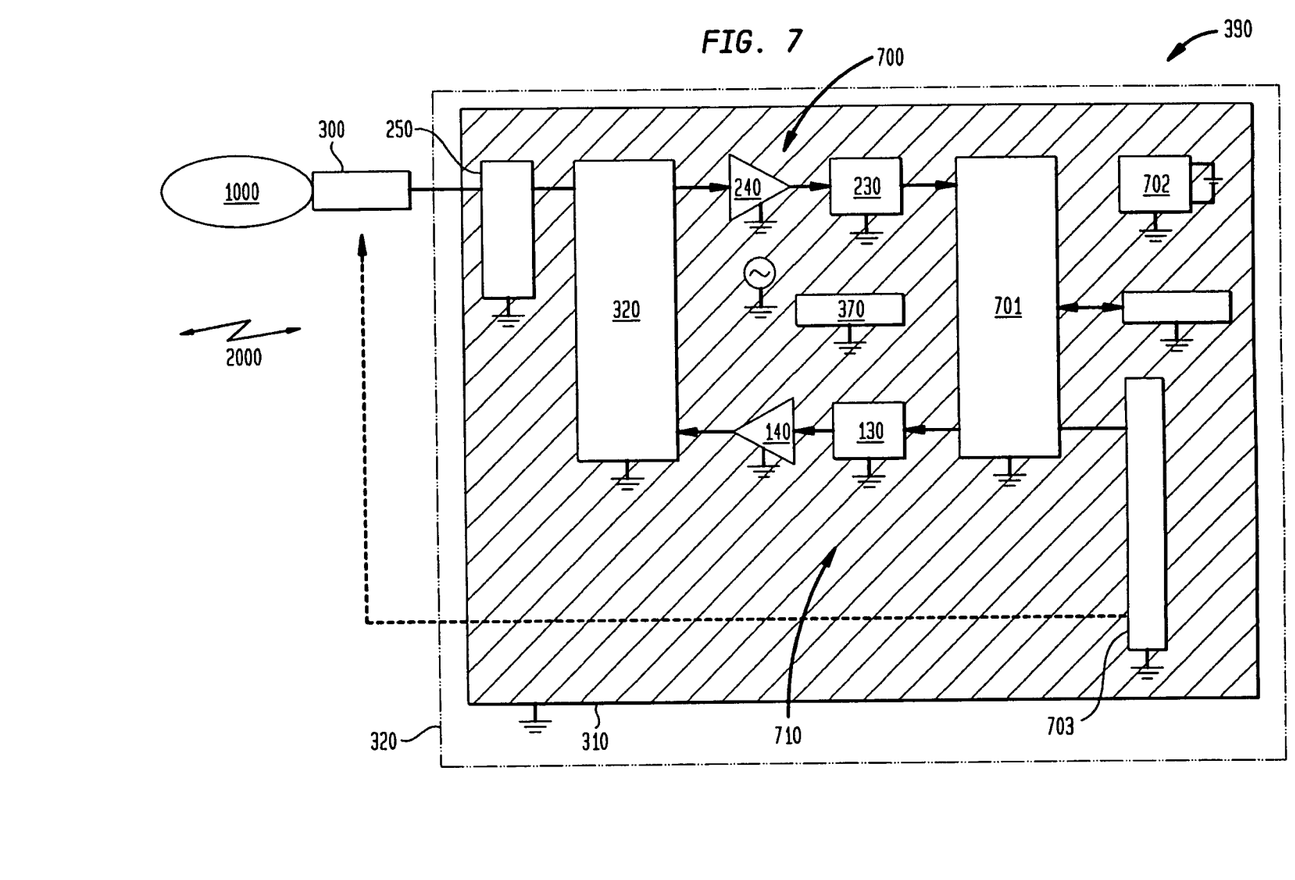
FIG. 7 is a schematic diagram of a device belonging to a short range communication system.

FIG. 7 illustrates a more complete implementation of a wireless controller device 390 according to embodiments of the present invention. Besides the receiver 700 and transmitter 710 blocks, it incorporates a dedicated processor 701 and power supply 702 (which may comprise of batteries). In this arrangement, the PCB ground plane 310 of the whole electronic system is used as the isolated surface element. On human interaction, the contact element 300 is operative, for example, on pressing a pushbutton by finger (e.g. for increasing the volume of a hearing aid system). (The PCB 310 itself, accordingly acts as the isolated conducting element). A keypad 703 is composed of pushbuttons which are integrated physically under the contact surface elements 300 and mechanically coupled with them.

A particularly useful application of certain embodiments of the present invention is to the bilateral hearing device situation. The devices may be hearing aids, or external units for communications with implanted devices. Bilateral devices may be used together, for example for improved noise reduction, or to allow the delivery of coordinated timing or other stimulation strategies. It is accordingly useful for them to be able to communicate directly with each other. A suitable implementation of embodiments of the present invention is well adapted to achieve this. In such an arrangement, it is desirable that the conductive surfaces of the bilateral devices are oriented the same way, so as to maximize efficiency. For BTE devices, the orientation with the plane of the isolated element facing towards the head is suitable, which is also convenient from the perspective of the PCB location. This arrangement will have a vertically polarized signal in the far field for each device, with the PCB correctly oriented for the polarization of the signal.

Implementations of embodiments of the present invention accordingly provide lower power requirements, thereby improving battery life, and reduced antenna size relative to other alternatives, while providing adequate bandwidth and quality of communications.

It will be appreciated that embodiments of the present invention is applicable to many different devices and situations, and may be implemented in a wide variety of ways. Embodiments of the present invention allow for effective, low cost communications between body worn medical devices, for example between BTE devices and a wireless controller and even between body worn and implanted devices. Additions and variations are within the scope of the present invention.

Further features and advantages of the present invention are described in Australian Provisional Application No. 2007905584, filed Oct. 12, 2007, entitled "Short range communications for body contacting devices." The above application is hereby incorporated by reference herein.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents. All patents and publications discussed herein are incorporated in their entirety by reference thereto.

What is claimed is:

1. A communication system for wirelessly transmitting at least one signal, the system comprising:
    a first device configured to receive and modulate the at least one signal, the first device having a first conductive element operatively adapted to contact a first human body, the first conductive element configured to wirelessly transmit the modulated signal by conduction through at least the first human body, the first device further including a second conductive element isolated from the first human body, the second conductive element configured to wirelessly transmit the modulated signal by EM signal propagation, the first device further including a modulator unit in communication with the first and second conductive elements, the modulator unit configured to receive the at least one signal, modulate the at least one signal, and provide the at least one modulated signal to the first and second conductive elements; and
    a second device having a first conductive element operatively adapted to contact a second human body, the first conductive element of the second device configured to receive the modulated signal wirelessly transmitted by conduction through at least the first human body from the first conductive element of the first device, the second device further including a second conductive element conductively isolated from the second human body, the second conductive element of the second device configured to receive the modulated signal wirelessly transmitted by EM signal propagation from the second conductive element of the first device.

2. The system of claim 1, wherein the second device is further configured to demodulate the received signal and to output the at least one signal.

3. The system of claim 1, wherein the first human body and the second human body are the same human body.

4. The system of claim 1, wherein the modulated signal is transmitted in at least one of the decimeter or centimeter frequency bands.

5. The system of claim 1, wherein the first and second conductive elements of the first device are connected by a first impedance matching circuit and wherein the first and second conductive elements of the second device are connected by a second impedance matching circuit.

6. The system of claim 5, wherein the impedance matching circuits each comprises a balun.

7. The system of claim 1, wherein the first and second devices are components of a medical device system.

8. The system of claim 7, wherein the second device is implanted in a recipient of the medical device system.

9. The system of claim 1, wherein the first device is a hearing prosthesis.

10. A transmitter device for wirelessly transmitting at least one signal to a receiver, the transmitter device comprising:
    a first module configured to receive the at least one signal;
    a second module configured to modulate the at least one signal; and
    a third module comprising:
        a first conductive element operatively adapted to contact a human body, wherein the first conductive element is positioned on an outer portion of the transmitter device, and
        a second conductive element, wherein the second conductive element is positioned inside of the transmitter device such that it is configured to be conductively isolated from the human body when the first conductive element of the transmitter device is in contact with the human body,
    wherein the first and second elements operate to wirelessly transmit the modulated signal to the receiver.

11. The transmitter of claim 10, wherein the modulated signal is transmitted in at least one of the decimeter and centimeter frequency bands.

12. The transmitter of claim 10, wherein the first and second conductive elements are connected by an impedance matching circuit.

13. The transmitter of claim 12, wherein the impedance matching circuit comprises a balun.

14. The transmitter of claim 10, wherein the transmitter is a component of a medical device system.

15. The transceiver of claim 10, wherein the transceiver is in contact with an ear of the human body and the receiver is in contact with a hand of the human body.

16. A method for wireless communication between a first device and a second device, comprising:

receiving at least one signal at the first device for transmission to the second device;

modulating at the first device the at least one signal; and wirelessly transmitting to the second device the modulated signal via first and second conductive elements, the first conductive element contacting a human body at an outer portion of the first device and a second conductive element positioned inside the first device and conductively isolated from the human body.

17. The method of claim 16, further comprising: receiving by the second device the transmitted modulated signal.

18. The method of claim 17, further comprising:

demodulating the received signal at the second device; and outputting by the second device the at least one signal.

19. The method of claim 16, wherein wirelessly transmitting the modulated signal comprises:

transmitting the modulated signal in at least one of the decimeter and centimeter frequency bands.

20. The method of claim 14, wherein the first device is a hearing prosthesis.

21. A wireless communications device comprising:

a first conductive element comprising a conductive plate associated with an outer housing of the wireless communications device such that the first conductive element is configured to be in operative contact with a human body;

a second conductive element inside the outer housing of the wireless communications device and configured to be operatively isolated from the human body when the first conductive element is in operative contact with the human body; and circuitry inside the wireless communications device connected to the first and second conductive elements and configured to at least one of wirelessly transmit and receive a signal via both the first and second conductive elements.

22. The wireless communications device of claim 21, wherein the circuitry inside the wireless communications device connected to the first and second conductive elements includes an impedance matching device.

23. The wireless communications device of claim 22, wherein the wireless communications device is one of a behind-the-ear hearing aid device or an in-the-ear hearing aid device.

* * * * *